United States Patent

Mathys, Sr. et al.

[11] Patent Number: 5,571,202
[45] Date of Patent: Nov. 5, 1996

[54] SHAFT FOR AN ARTICULATION ENDOPROSTHESIS

[75] Inventors: Robert Mathys, Sr.; Robert Mathys, Jr., both of Bettlach; Beat Gasser, Ittigen, all of Switzerland

[73] Assignee: Mathys AG Bettlach, Bettlach, Switzerland

[21] Appl. No.: 307,562

[22] PCT Filed: Jan. 19, 1993

[86] PCT No.: PCT/CH93/00008

§ 371 Date: Sep. 19, 1994

§ 102(e) Date: Sep. 19, 1994

[87] PCT Pub. No.: WO94/16649

PCT Pub. Date: Aug. 4, 1994

[51] Int. Cl.⁶ ............................................. A61F 2/32
[52] U.S. Cl. ................................... 623/23; 623/18
[58] Field of Search .......................... 623/23, 16, 18, 623/22

[56] References Cited

U.S. PATENT DOCUMENTS

| 3,781,917 | 1/1974 | Mathys | 623/23 |
|---|---|---|---|
| 3,893,196 | 7/1975 | Hochman | 623/23 |
| 4,146,936 | 4/1979 | Aoyagi et al. | 623/23 |
| 4,454,612 | 6/1984 | McDaniel et al. | |
| 4,599,085 | 7/1986 | Riess et al. | 623/23 |
| 4,750,905 | 6/1988 | Koeneman et al. | 623/23 |
| 4,902,297 | 2/1990 | Devanathan | 623/23 |
| 5,152,794 | 10/1992 | Davidson | 623/23 |
| 5,156,628 | 10/1992 | Kranz | 623/23 |
| 5,176,712 | 1/1993 | Homsy | 623/23 |
| 5,181,930 | 1/1993 | Dumbleton et al. | 623/23 |
| 5,314,492 | 6/1994 | Hamilton et al. | 623/23 |

FOREIGN PATENT DOCUMENTS

| 0484082 | 5/1992 | European Pat. Off. |
| 2199967 | 4/1974 | France . |
| 29 33 237 | 3/1981 | Germany . |
| 35 25 547 | 1/1987 | Germany . |
| 38 40 475 | 6/1990 | Germany . |
| 2045082 | 10/1980 | United Kingdom . |
| WO86/06617 | 11/1986 | WIPO . |

*Primary Examiner*—John G. Weiss
*Assistant Examiner*—Bruce E. Snow
*Attorney, Agent, or Firm*—Walter C. Farley

[57] ABSTRACT

A shaft for an articulation endoprosthesis has a metallic core (1), a proximally connected neck part (10) and an envelope (2) made of a non-metallic, elastic material that distally surrounds the core. Adherence between the core (1) and the envelope is ensured by a form fit and/or by a frictional connection. The non-metallic material of the envelope has a modulus of elasticity between 500 and 10,000 N/mm². The envelope is provided with an additional superficial layer (3) made of biocompatible material having thickness of less that 600 μm and a higher surface hardness than the envelope (2).

32 Claims, 2 Drawing Sheets

SHAFT FOR AN ARTICULATION ENDOPROSTHESIS

FIELD OF INVENTION

This invention concerns a shank or shaft for an articulation or joint-endoprosthesis and a component of a joint-endoprosthesis with such a shank.

BACKGROUND OF THE INVENTION

Joint endoprostheses, especially for hip-joints, consist of an acetabular shell component and of a femur component insertable by its shank into the tubular femur.

Femur components for hip prostheses already are known that consist essentially of a metal core and a surrounding plastic sheath. This design offers the advantage of behaving similarly elastically to the bone structure to be replaced.

However, this kind of femur component entails the problem of an unprotected sheath polymer surface from which residual monomers may be released to possibly form a thin reticular bonding layer between the plastic sheath and the bone.

SUMMARY OF THE INVENTION

An object of the invention is to provide a shank for a joint-endoprosthesis which on one hand offers improved elastic behavior matching the physiological needs of the bone in such a way that the shank flexibility, when subject to bending, approximates that of the natural bone and allows gradual load transfer from the shank to the enclosing bone, and on the other hand offers improved biocompatibility. Furthermore, the invention solves the problem of endowing a joint-endoprosthesis with improved surface hardness.

Essentially, the advantages of the invention are that, thanks to the surface layer of the invention, the shank bio-compatibility is improved as a whole and that direct and firm contact between the shank and the bone is made possible. Depending on the kind of bio-compatible surface layer, bone growth can be induced, thereby improving the primary stability, that is the initial anchoring, and thus accelerating the healing stage.

In a preferred embodiment of the invention, the shank is fitted with one or more boreholes in the proximo-lateral area, that is at the outer side of its upper end. These boreholes serve to anchor by screws the prosthesis shank in the proximal area of the outer cortex. Such a screw may be rotated from above, that is from the side of the prosthesis neck, i.e., from the prosthesis collar, through the borehole laterally into the bone where it is thereby anchored. However, the borehole also may be internally threaded and the screw may be rotated from below, that is laterally into the inner thread, the resting surface of the screw on the outer cortex being enlarged as called for by using a washer. On one hand these screws enhance security against shank rotation inside the marrow duct and on the other hand they contribute synergistically together with the triple-layer design of the prosthesis shank of the invention to a gradual load transfer from the shank to the bone.

BRIEF DESCRIPTION OF THE DRAWINGS

The invention and further developments thereof are elucidated below with reference to an illustrative embodiment.

DESCRIPTION OF THE PREFERRED EMBODIMENTS

Figure 1:
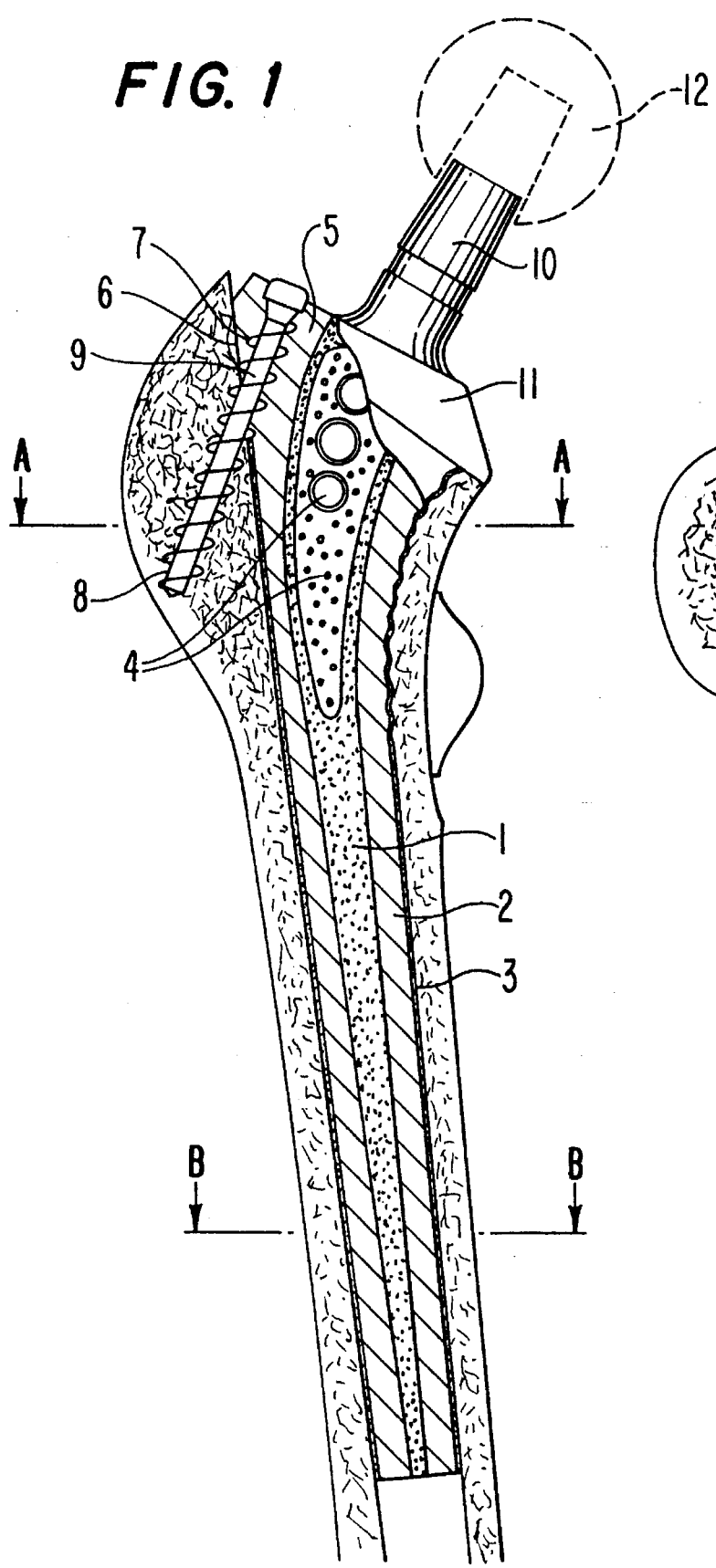
FIG. 1 is a longitudinal section of a shank of the invention inserted in a thighbone.
Figure 2:
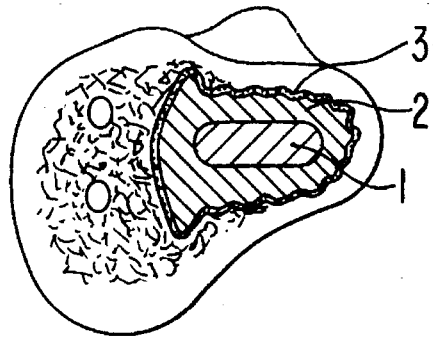
FIG. 2 is a cross-section along line A—A of the proximal portion of the shank of FIG. 1.
Figure 3:
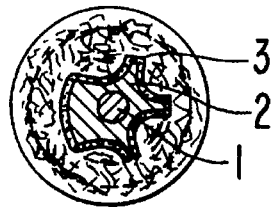
FIG. 3 is a cross-section along line B—B of the distal portion of the shank of FIG. 1.

The femur component of a hip-joint prothesis shown in FIGS. 1–3 essentially consists of the triple-stratum shank 1, 2, 3 of the invention which continues into a conical neck part 10 that can receive a plug-on swivel ball 12. As regards other types of hip-joint protheses, the swivel joint also may be rigidly affixed to the neck part 10 and form one unit with the shank.

The sandwich-type shank 1, 2, 3 consists of a titanium or titanium-alloy core 1 imbedded in a biocompatible, thermoplastic (for instance POM, PEEK, PEI or the like) sheath 2. The two materials, namely metal and plastic, are well bounded and kept together in geometrically or frictionally locking manner. This feature is enhanced by the comparatively small (blind) and comparatively large (through-) holes 4 in the core 1, said holes seating pin-shaped extensions of the sheath 2. The sheath 2 can be deposited by injection-molding, bonding and/or post-mechanical processing of its plastic.

Comprehensive experiments have shown that when optimally selecting the volume ratio $V_k/V_m$ of the core 1 to the sheath 2, especially good elastic shank behavior is achieved regarding the local, physiological requirements of the bone. Advantageously, the ratio $V_k/V_m$ is in the range of 0.15 to 0.60, and preferably between 0.25 and 0.4. As shown by a comparison of the two cross-sections of the proximal and distal portions of the shank (FIGS. 2 and 3 resp.), the volume ratio in these two portions does vary. In the distal shank portion, which is two-thirds of the total shank length, the volume ratio of the core 1 to the sheath 2 should be in the range of 0.10 to 0.45, preferably between 0.2 and 0.3. The core may be configured being both centered and eccentric within the prosthesis shank, that is, the center axes of the core and the sheath need not necessarily coincide. Depending on the design of the prosthesis shank, an eccentrically configured core may be advantageous for optimal, gradual load distribution and transfer. The non-metallic material of the sheath preferably has a Young's modulus between 500 and 10,000 N/mm$^2$.

The plastic sheath 2 is enclosed in turn by a comparatively thin surface layer 3 (maximally 600 μ, preferably thinner than 200 μ) consisting of a bio-compatible material and evincing a complex structure at its outside. Preferably the surface layer is free of internal pores. Surface layer 3 can be a compound layer wherein the matrix of the compound layer consists of the same material as the sheath.

A plastic macro-structure with a roughness depth of 0.2 to 2.5 mm, preferably between 0.5 and 1.5 mm, is present in the sheath 2 in the proximal shank portion amounting to one third the total shank length (measured in the distal direction from the neck portion 10). A microstructure with a roughness depth between 0.1 and 500.0μ, preferably between 5 and 80μ, is present in the distal shank portion amounting to two-thirds of the total shank length (measured in the proximal direction from the shank tip).

Furthermore, through the surface layer, a microstructure with a roughness depth between 0.1 and 500.0μ, preferably between 5 and 300μ may also be present in the proximal shank portion in addition to the macro-structure. A roughness depth between 5 and 100μ or between 150 and 300μ to enhance surface roughness is especially advantageous.

Pure titanium, titanium alloys in particular $TiAl_6V_4$, $TiAl_5Fe_{2.5}$ or $TiAl_6Nb_7$ are applicable as bio-compatible materials for the core 1 of the shank of the invention. Such polymers as polyoxymethylene (POM), polyether-etherketone (PEEK), polyaryletherketone (PAEK), polyetherimide (PEI), polymethylpentene (PMP), polysulfone (PSU), polyethersulfone (PESU or PES), polyethylene terephthalate (PETP), polymethylmethacrylate (PMMA), ultrahigh molecular-weight polyethylene (UHMW-PE) or liquid crystal polymers (LCP) are suitable for the sheath 2 of the shank of the invention.

Biological glasses, calcium phosphates, in particular hydroxyl apatite, combinations thereof, pure titanium, titanium alloys in particular $TiAl_6V_4$, $TiAl_5Fe_{2.5}$ or $TiAl_6Nb_7$ or combinations of one of these materials with the plastic sheath material serving as a matrix are suitable for the surface layer.

The plastic and surface-layer materials of the two structures, namely the sheath 2 and the surface layer 3, are clearly bounded relative to each other, that is, they lack a clear transition zone (mixture). Even when the particles of the material of the surface layer 3 are imbedded in the course of manufacture into the plastic (matrix) sheath 2, the thickness of this surface compound layer 3 is well defined (FIG. 5) because it consist of that layer containing such particles, whereas the sheath 2 is composed of a pure plastic free of any particles.

Figure 4:
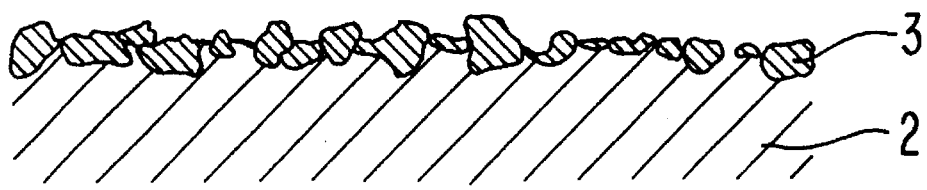
FIG. 4 schematically shows the surface layer of the shank of FIG. 1 for the illustration of a particulate layer when this surface layer consists of a uniform material.
Figure 5:
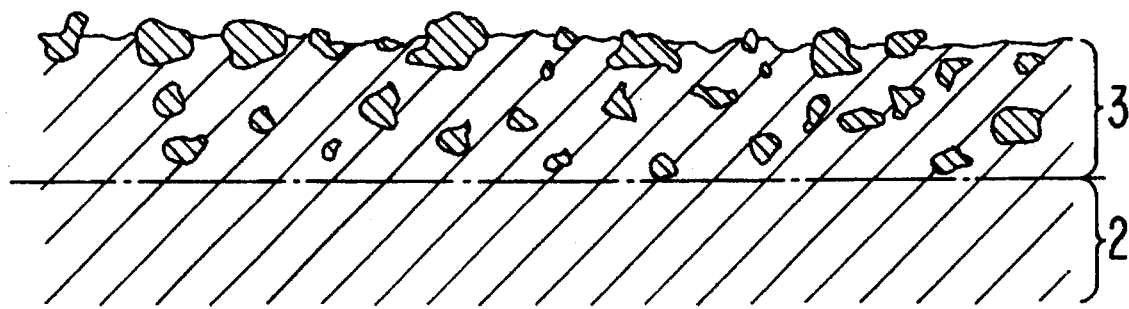
FIG. 5 schematically shows the surface layer of the shank of FIG. 1 when it is a particle layer of compound nature.

The material of the surface layer 3 may be homogeneous or it may consist of several materials. Compared with the two other structures, namely the core 1 and the sheath 2, the surface layer 3 is thin, as a result of which the surface layer 3 does not affect the overall mechanical shank properties. If this surface layer 3 is made of a homogeneous material, it will be a single layer, as shown in FIG. 4 illustrating a particle layer. In this case the individual particles are not interlinked, being merely bonded to the substrate, that is to the plastic sheath 2. On the other hand if this surface layer 3 consists of a mixture of materials, it may be considered being stratified as shown in FIG. 5 for a compound particle layer. In the latter variation of the surface layer 3, the individual particles again are held together solely by the plastic matrix preferably consisting of the same material as the sheath 2.

The surface layer 3 can be deposited on the sheath 2 by a number of different known methods such as evaporation (physical, chemical vapor deposition PVD/CVD), cold pressing, hot pressing, flame plating, plasma spraying, laser treatment, sintering, shrinking, injection molding, diffusion or ultrasonic coating or the like.

As shown by FIG. 1, a borehole 6 is present in the proximo-lateral area 5 of the shank of the invention to allow anchoring a screw 9 in the outer cortex 8 of the thigh bone. The screw 9 may be a tension screw with a long shank or a fully threaded screw. For both types of screw a geometric locking is achieved between the prosthesis collar 11 and the thighbone. When the screw 9 is fully threaded and anchored in the prosthesis collar and the bone, the connection between bone and prosthesis is firmer mechanically because displacements between the screw 9 and the bone as well as the prosthesis collar are prevented. Furthermore, screw 9 also may be inserted reversely, that is laterally from below into the inside thread 7 of borehole 6, in which case the surface on which the screwhead rests on the outer cortex is appropriately enlarged by a washer.

Core 1 projects upwardly out of sheath 2 and forms a conical neck position 10 seating swivel balls 12 of various sizes which comprise matching conical cavities and are plugged onto said portion 10.

The above described shank of the invention for use as hip-joint replacement moreover may be used to replace other joints such as shoulder or finger joints.

We claim:

1. A shank for a joint endoprosthesis comprising
    a metal core (1) having a proximal end, a distal portion and a neck portion (10) joined to said proximal end;
    a non-metallic, elastic sheath (2) enclosing said distal portion of said core and having an outer surface,
        said sheath having a Young's modulus between 500 and 10,000 $N/mm^2$,
        said core and sheath being geometrically or frictionally held together,
        said outer surface of essentially one-third of the length of said sheath adjacent said proximal end having a macro-structure with a roughness depth of between 0.2 and 2.5 mm, and
        said outer surface of essentially two thirds of the length of said sheath in said distal portion having a micro-structure with a roughness depth of between 0.1 and 500 μ; and
    a surface layer (3) on said outer surface of said sheath, said surface layer comprising a bio-compatible material free of inner pores, said surface layer having a thickness of less than 600 μm and a surface hardness greater than said sheath.

2. A shank according to claim 1 wherein said non-metallic sheath comprises a homogeneous material.

3. A shank according to claim 1 wherein said nonmetallic sheath comprises a compound material.

4. A shank according to claim 1 wherein said sheath and surface layer are frictionally held together.

5. A shank according to claim 1 wherein said surface layer has a thickness of less than 200μ.

6. A shank according to claim 5 wherein said surface layer has a thickness of less than 100μ.

7. A shank according to claim 1 wherein said surface layer is a compound layer having a matrix comprising a material of said sheath.

8. A shank according to claim 7 wherein said surface layer (3) has a thickness of less than 400μ.

9. A shank according to claim 8 wherein said surface layer (3) has a thickness of less than 200μ.

10. A shank according to claim 1 wherein a volume ratio of the core volume to the sheath volume is between 0.15 and 0.60.

11. A shank according to claim 10 wherein a volume ratio of the core volume to the sheath volume is between 0.25 and 0.40.

12. A shank according to claim 1 wherein a volume ratio of the core volume to the sheath volume in two-thirds of the distal portion is between 0.10 and 0.45.

13. A shank according to claim 1 wherein a volume ratio of the core volume to the sheath volume in two-thirds of the distal portion is between 0.2 and 0.3.

14. A shank according to claim 1 wherein said core comprises a material selected from the group consisting of pure titanium, $TiAl_6V_4$, $TiAl_5Fe_{2.5}$, and $TiAl_6Nb_7$.

15. A shank according to claim 1 wherein said sheath (2) comprises a thermoplastic.

16. A shank according to claim 15 wherein said thermoplastic is selected from the group consisting of polyoxymethylene (POM), polyetheretherketone (PEEK), polyaryletherketone (PAEK), polyetherimide (PEI) and a liquid-crystal polymer (LCP).

17. A shank according to claim 16 wherein said thermoplastic is selected from the group consisting of polymethylpentene (PMP), polysulfone (PSU), polyethersulfone (PESU or PES), polyethylene terephthalate (PETP), polymethylmethacrylate (PMMA) and ultrahigh molecular-weight polyethylene (UHMW-PE).

18. A shank according to claim 1 wherein said outer surface of said one-third of said surface layer (3) comprises a macro-structure with a roughness depth of between 0.5 and 1.5 mm.

19. A shank according to claim 18 and further including a micro-structure in said outer surface of said sheath along essentially one-third of said core adjacent said proximal end, said micro-structure having a roughness depth of between 0.1 and 500μ.

20. A shank according to claim 18 and further including a micro-structure in said outer surface of said sheath along essentially one-third of said core adjacent said proximal end, said micro-structure having a roughness depth of between 0.1 and 500μ.

21. A shank according to claim 20 wherein said roughness depth is between 5 and 100μ.

22. A shank according to claim 20 wherein said roughness depth is between 5 and 300μ.

23. A shank according to claim 1 wherein said outer surface of said sheath along said two-thirds of said core comprises a micro-structure with a roughness depth of between 5 and 80μ.

24. A shank according to claim 1 wherein said surface layer comprises one or more of the materials selected from the group consisting of pure titanium, a titanium alloy, a biological glass, a calcium phosphate and hydroxyl apatite.

25. A shank according to claim 1 wherein said surface layer is a compound layer having a matrix comprising sheath material and with imbedded particles comprising one or more of the materials selected from the group consisting of pure titanium, a titanium alloy, a biological glass, calcium phosphate and hydroxyl apatite.

26. A shank according to claim 25 wherein said particles imbedded therein are separated from each other.

27. A shank according to claim 1 wherein said core includes means defining recesses therein.

28. A shank according to claim 27 wherein said recesses include holes passing through said core and said sheath.

29. A shank according to claim 1 and comprising a collar (11) at a proximal end of said shank.

30. A shank according to claim 1 and comprising an internally threaded hole (6) in a proximo-lateral portion (5) of said shank to receive a screw (9) for anchoring said shank in an outer cortex of a bone.

31. A shank according to claim 1 wherein said core is eccentrically received in said sheath.

32. A shank according to claim 1 and including a swivel ball (12) mounted on said neck portion (10).

* * * * *